United States Patent
Chen et al.

(10) Patent No.: US 12,406,764 B2
(45) Date of Patent: Sep. 2, 2025

(54) METHOD FOR DETERMINING CILIARY BEAT FREQUENCY

(71) Applicant: Anivance AI Corporation, Hsinchu County (TW)

(72) Inventors: Guan-Yu Chen, Zhubei (TW); Ren-Hao Xie, Zhubei (TW); Shiue-Luen Chen, Yuanshan Township (TW)

(73) Assignee: Anivance AI Corporation, Hsinchu County (TW)

( * ) Notice: Subject to any disclaimer, the term of this patent is extended or adjusted under 35 U.S.C. 154(b) by 385 days.

(21) Appl. No.: 18/312,839

(22) Filed: May 5, 2023

(65) Prior Publication Data

US 2023/0386645 A1    Nov. 30, 2023

(30) Foreign Application Priority Data

May 24, 2022   (TW) .................................. 111119251

(51) Int. Cl.
*G06K 9/00*      (2022.01)
*G06T 5/70*      (2024.01)
(Continued)

(52) U.S. Cl.
CPC ............... *G16H 30/40* (2018.01); *G06T 5/70* (2024.01); *G06T 7/0012* (2013.01); *G06T 7/73* (2017.01);
(Continued)

(58) Field of Classification Search
CPC .......... G16H 30/40; G16H 50/20; G06T 5/70; G06T 7/0012; G06T 7/73;
(Continued)

(56) References Cited

U.S. PATENT DOCUMENTS 9,483,685 B2 *  11/2016  Chennubhotla ...... G06V 10/758
10,241,028 B2 *   3/2019  Rowe .................... G01J 9/02
(Continued)

FOREIGN PATENT DOCUMENTS

| CN | 201019775 Y | * | 2/2008 | ............... G06T 7/70 |
| KR | 100244033 B1 | * | 2/2000 | ............ A61B 10/02 |
| KR | 100517120 B1 | * | 9/2005 | ............... G06T 7/70 |

OTHER PUBLICATIONS

P. Sampaio et al., "CiliarMove: new software for evaluating ciliary beat frequency helps find novel mutations by a Portuguese multi-disciplinary team on primary ciliary dyskinesia," ERJ Open Research, 7, pp. 1-12, Jan. 2021.
(Continued)

*Primary Examiner* — Shervin K Nakhjavan
(74) *Attorney, Agent, or Firm* — Winston Hsu

(57) ABSTRACT

A method includes steps of: determining a frame rate and a video resolution of a video; selecting N number of frames from the video; performing image denoising on the N number of frames to obtain N number of denoised images; determining a plurality of target positions that correspond to a plurality of ciliary beat patterns based on commonly-located pixels of the N number of denoised images; and for each ciliary beat pattern, determining peak values among the N number of grayscale values, and determining a ciliary beat frequency based on the peak values.

10 Claims, 3 Drawing Sheets

(51) Int. Cl.
  *G06T 7/00*   (2017.01)
  *G06T 7/73*   (2017.01)
  *G16H 30/40*  (2018.01)

(52) U.S. Cl.
  CPC ............... *G06T 2207/10016* (2013.01); *G06T 2207/20076* (2013.01)

(58) Field of Classification Search
  CPC . G06T 2207/10016; G06T 2207/20076; G06T 2207/20056; G06T 7/262
  See application file for complete search history.

(56) References Cited

U.S. PATENT DOCUMENTS 10,942,112 B2 *  3/2021  Rowe .................... G01B 9/0205
12,361,668 B2 *  7/2025  Kim ...................... G06V 10/761

OTHER PUBLICATIONS

R. Nakamura et al., "A novel method for live imaging of human airway cilia using wheat germ agglutinin," Scientific Reports, Sep. 10, 2020.

* cited by examiner

METHOD FOR DETERMINING CILIARY BEAT FREQUENCY

CROSS-REFERENCE TO RELATED APPLICATION

This application claims priority to Taiwanese Invention Patent Application No. 111119251, filed on May 24, 2022.

FIELD

The disclosure relates to a method for determining a ciliary beat frequency, and more particularly to a method for determining a ciliary beat frequency based on a video of ciliary movement.

BACKGROUND

Human bronchus is lined with respiratory cilia that generally beat at a frequency ranging from 8 to 20 Hz, and that move pollutants, sputum and mucus up and out of human airways. A conventional approach to determine a ciliary beat frequency is to capture a video of ciliary movement using microscopy with a charge-coupled device (CCD) detector, observe the ciliary movement with naked eyes, and then roughly estimate the ciliary beat frequency based on experience. However, such approach is time consuming, labor intensive and error-prone.

SUMMARY

Therefore, an object of the disclosure is to provide a method for determining a ciliary beat frequency based on a video of ciliary movement that can alleviate at least one of the drawbacks of the prior art.

According to the disclosure, the video contains a series of consecutive frames. The method includes steps of:
  determining a frame rate of the video and a video resolution of the video;
  selecting, based on the frame rate, N number of frames from the series of consecutive frames of the video, where N is a positive integer greater than one;
  performing image denoising on the N number of frames to obtain N number of denoised images, respectively, each of the N number of denoised images having a resolution equal to the video resolution;
  determining a plurality of target positions that respectively correspond to a plurality of ciliary beat patterns, wherein, for every N number of commonly-located pixels respectively of the N number of denoised images, when it is determined that N number of grayscale values respectively of the N number of commonly-located pixels are not the same, a position of the N number of commonly-located pixels is determined as one of the target positions, and the N number of grayscale values of the N number of commonly-located pixels at said one of the target positions represent the respective one of the ciliary beat patterns;
  for each of the ciliary beat patterns, determining peak values among the N number of grayscale values; and
  for each of the ciliary beat patterns, determining a ciliary beat frequency based on the peak values thus determined.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
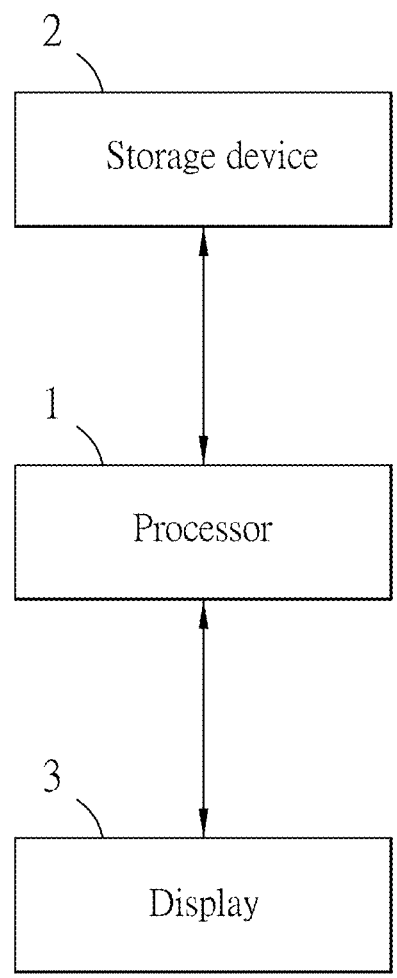
FIG. 1 is a block diagram illustrating a system for determining a ciliary beat frequency according to an embodiment of the disclosure.

Referring to FIG. 1, an embodiment of a system for determining a ciliary beat frequency based on a video of ciliary movement according to the disclosure is illustrated. The system includes a processor 1, a storage device 2 and a display 3. The processor 1 is electrically connected to the storage device 2 and the display 3.

The processor 1 may be implemented by a central processing unit (CPU), a microprocessor, a micro control unit (MCU), a system on a chip (SoC), an application specific integrated circuit (ASIC) for image processing, or any circuit configurable/programmable in a software manner and/or hardware manner to implement functionalities discussed in this disclosure.

Figure 3:
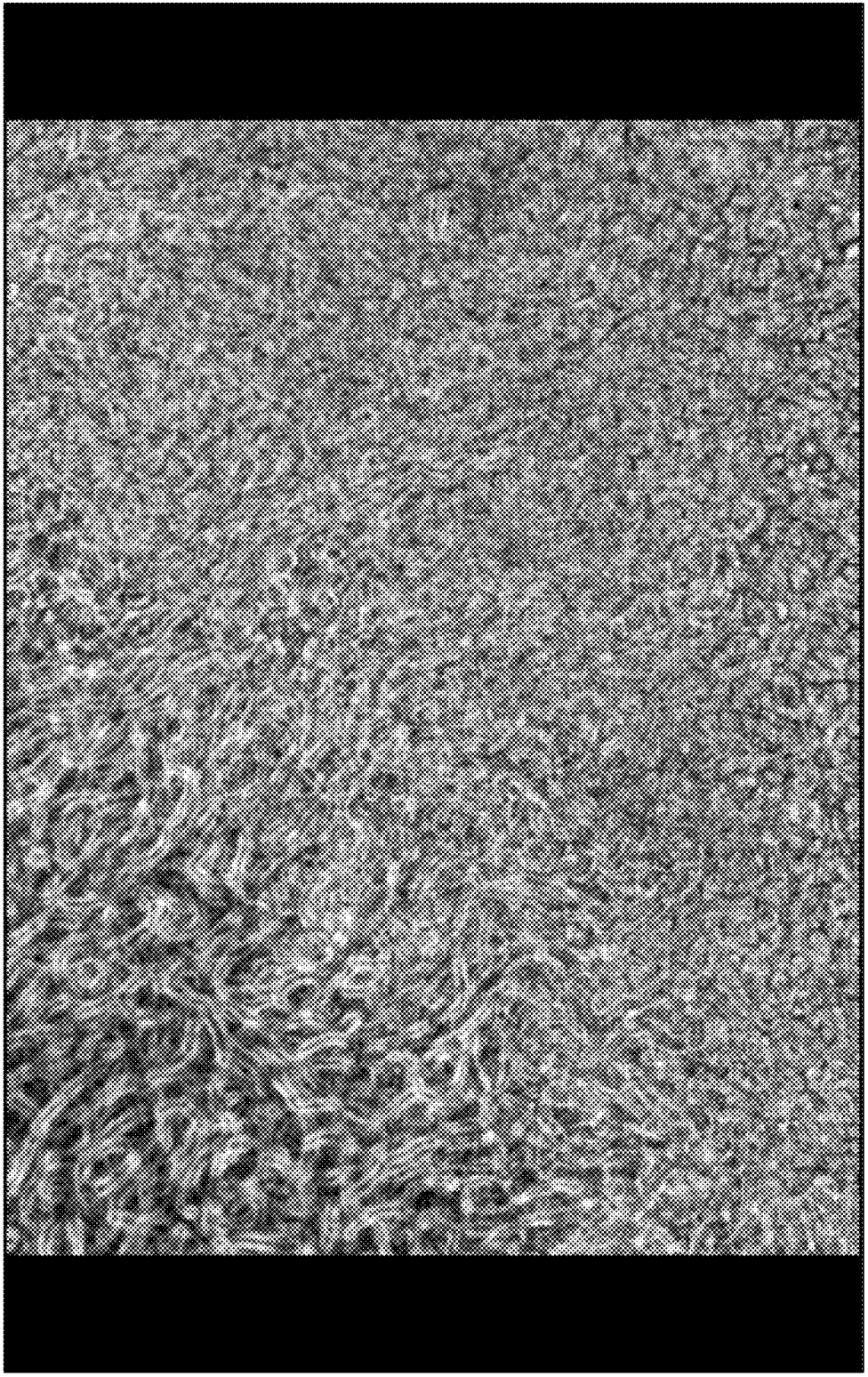
FIG. 3 shows an example of a frame of a video of ciliary movement.

The storage device 2 may be implemented by random access memory (RAM), double data rate synchronous dynamic random access memory (DDR SDRAM), read only memory (ROM), programmable ROM (PROM), flash memory, a hard disk drive (HDD), a solid state drive (SSD), electrically-erasable programmable read-only memory (EEPROM) or any other volatile/non-volatile memory devices, but is not limited thereto. The storage device 2 is configured to store a video of ciliary movement. The video contains a series of consecutive frames, one of which is exemplarily shown in FIG. 3. Each pixel in each frame of the video has a grayscale value ranging from 0 to 255. The video has a file format of MPEG-4 Part 14 (MP4) in this embodiment, but the file format of the video is not limited thereto.

The display 3 may be a liquid-crystal display (LCD), a light-emitting diode (LED) display, a plasma display panel, a projection display or the like. However, implementation of the display 3 is not limited to the disclosure herein and may vary in other embodiments.

Figure 2:
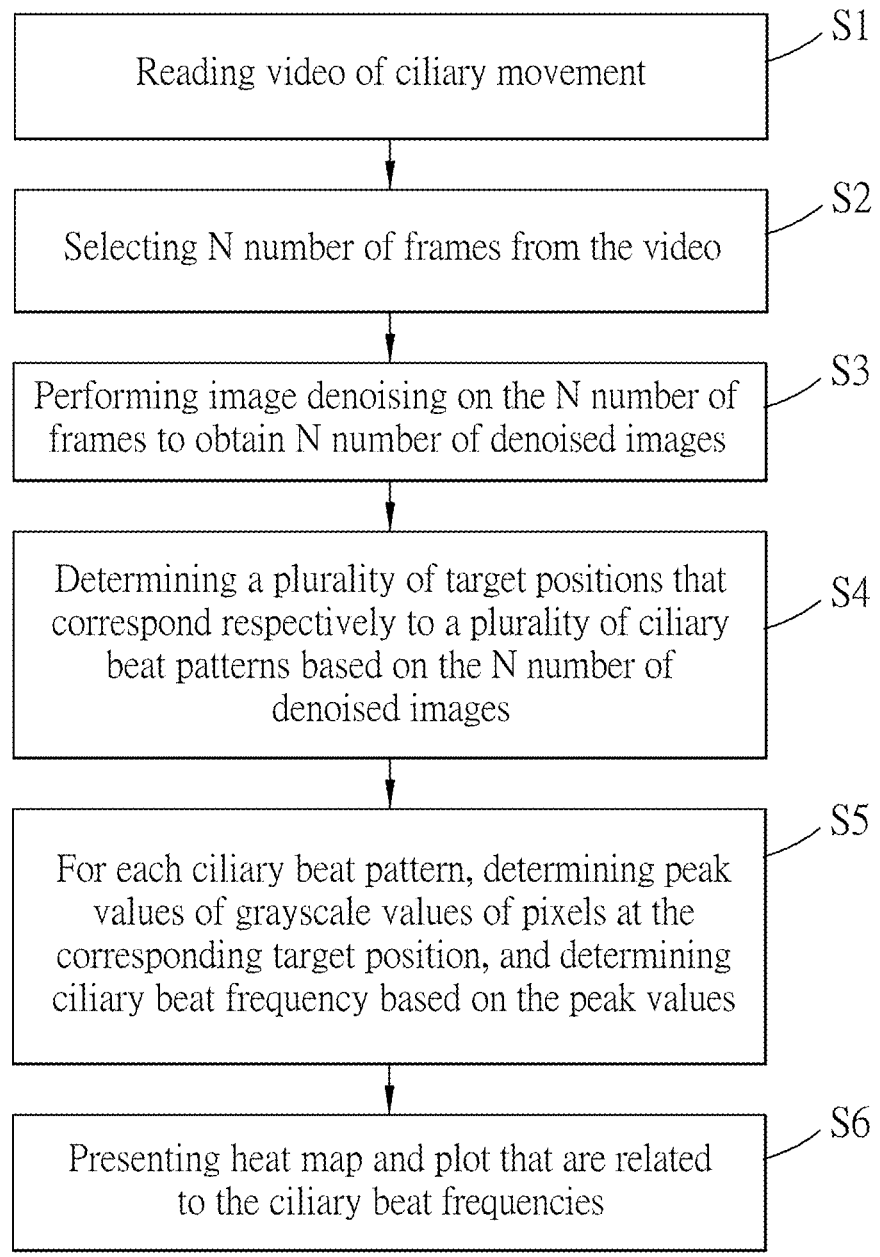
FIG. 2 is a flow chart illustrating a method for determining a ciliary beat frequency according to an embodiment of the disclosure.

Referring to FIG. 2, a method for determining a ciliary beat frequency based on a video of ciliary movement is illustrated. The method is to be implemented by the processor 1 of the system that is previously described, and is realized in a MATLAB platform. The method includes steps S1 to S6 delineated below.

In step S1, the processor 1 accesses the storage device 2 to read the video from the storage device 2, and determines a frame rate and a video resolution of the video. For example, the frame rate of the video is 100 frames per second (FPS), and the video resolution of the video is 1440×1080 pixels.

In step S2, the processor 1 selects, based on the frame rate determined in step S1, N number of frames from the series of consecutive frames of the video, where N is a positive integer greater than one. In particular, the processor 1 selects first N number of consecutive frames of first X seconds (e.g., 0.3 seconds) of the video, where N is equal to a product of X and the frame rate. In the case that the frame rate is 100 FPS, first thirty frames (i.e., N=0.3×100=30) will be selected. It is worth to note that the thirty consecutive frames correspond to the zeroth second, the 0.01 second, the 0.02 second, . . . and the 0.3 second of the video, respectively.

That is to say, a time interval between any consecutive two of the thirty frames is 0.01 seconds.

In step S3, the processor 1 performs image denoising on the N number of frames to obtain N number of denoised images, respectively. Each of the N number of denoised images has a resolution equal to the video resolution (i.e., 1440×1080 pixels).

Specifically, denoising of step S3 includes the following operations. First, the processor 1 performs image smoothing on the N number of frames to result in N number of smoothed images, respectively. Specifically, for each pixel of each of the N number of frames (referred to as "to-be-processed pixel"), the processor 1 calculates an average of grayscale values respectively of the to-be-processed pixel and surrounding pixels that are located within a predetermined range of the to-be-processed pixel, and replaces a grayscale value of the to-be-processed pixel with the average of grayscale values. In this embodiment, the surrounding pixels are four pixels respectively to the immediate up, immediate down, immediate left and immediate right of the to-be-processed pixel. Assuming that the smoothed images define a two-dimensional coordinate system that is 1440 by 1080, and each pixel in each of the smoothed images is assigned a coordinate set that represents the position of the pixel within the corresponding smoothed image, then a pixel from one smoothed image is said to be commonly located with a pixel from another smoothed image if the coordinate sets assigned to these two pixels are identical. Subsequently, for every N number of commonly-located pixels respectively of the N number of smoothed images, the processor 1 determines the position of the N number of commonly-located pixels as a noise position when it is determined that N number of grayscale values respectively of the N number of commonly-located pixels are the same. For each of the N number of frames, the processor 1 replaces a grayscale value of a pixel corresponding to the noise position with a predetermined grayscale value (e.g., 0). In this way, the N number of denoised images (i.e., thirty denoised images) are obtained.

Assuming that the denoised images define a two-dimensional coordinate system that is 1440 by 1080, and each pixel in each of the denoised images is assigned a coordinate set that represents the position of the pixel within the corresponding denoised image, then a pixel from one denoised image is said to be commonly located with a pixel from another denoised image if the coordinate sets assigned to these two pixels are identical. In step S4, the processor 1 determines a plurality of target positions that respectively correspond to a plurality of ciliary beat patterns. In one embodiment, for every N number of commonly-located pixels respectively of the N number of denoised images, the processor 1 determines the position of the N number of commonly-located pixels as a target position when it is determined that N number of grayscale values respectively of the N number of commonly-located pixels are not the same, and the N number of grayscale values represent a corresponding ciliary beat pattern. Then, the processor 1 records N number of grayscale values of pixels, each of which is located at the target position, respectively of the N number of frames in a matrix (or in an array) in the MATLAB platform. Generally speaking, a number M of target positions (and hence a number M of ciliary beat patterns) will be determined, where M is an integer greater than one. For example, in a scenario where 10000 target positions (M=10000) that are respectively related to 10000 ciliary beat patterns are determined, a matrix having a dimension of 10000×30 is obtained. The matrix is expressed in a form of "[A1_1 A1_2 . . . A1_30; A2_1 A2_2 . . . A3_30; . . . Ai_j . . . ; A10000_1 A10000_2 . . . A10000_30]" in the MATLAB platform, where "Ai_j" represents a grayscale value of a pixel that is located at an $i^{th}$ target position in a $j^{th}$ frame, i is an integer ranging from 1 to 10000, and j is an integer ranging from 1 to 30. Each row of the matrix corresponds to a respective one of the 10000 ciliary beat patterns. That is to say, an $i^{th}$ row (hereinafter also referred to as "Ai") of the matrix corresponds to an $i^{th}$ one of the 10000 ciliary beat patterns, and the $i^{th}$ one of the 10000 ciliary beat patterns is located at an $i^{th}$ one of the 10000 target positions. For instance, the first row of the matrix (i.e., "[A1_1 A1_2 . . . A1_30]" or "A1") corresponds to a first one of the 10000 ciliary beat patterns, and the first one of the 10000 ciliary beat patterns is located at a first one of the 10000 target positions.

In step S5, for each ciliary beat pattern, the processor 1 first determines peak values among the N number of grayscale values by calling function "findpeaks" in the MATLAB platform, and then determines a ciliary beat frequency based on the peak values thus determined. Specifically, the processor 1 determines, for every consecutive two of the peak vales, an inter-peak time interval between the consecutive two of the peak vales, and calculates an average of the inter-peak time intervals obtained from all of the peak values. Then, the processor 1 calculates a reciprocal of the average of the inter-peak time intervals as the ciliary beat frequency for the ciliary beat pattern. For example, for each of the 10000 ciliary beat patterns (which respectively correspond to "A1", "A2", . . . , "A10000"), the processor 1 calls function "findpeaks" in the MATLAB platform to determine peak values for the ciliary beat pattern. For the ciliary beat pattern that corresponds to "A1", it is assumed that the grayscale values of "A1_7", "A1_15" and "A1_27" of "A1" are determined as the peak values in "A1"; since the time interval between any consecutive two frames among the thirty frames that respectively correspond to "A1_1", "A1_2" "A1_30" is 0.01 seconds, the processor 1 will determine that an inter-peak time interval between the peak values "A1_7" and "A1_15" is equal to 0.08 seconds, i.e., 0.01×(15-7)=0.08, and an inter-peak time interval between the peak values "A1_15" and "A1_27" is equal to 0.12 seconds, i.e., 0.01×(27-15)=0.12. Subsequently, the processor 1 would calculate the average of the inter-peak time intervals thus determined to be equal to 0.1 seconds, i.e., (0.08+0.12)÷2=0.1, and calculate the reciprocal of the average of the inter-peak time intervals to be equal to Hz (i.e., 0.1-1=10), which serves as the ciliary beat frequency of the ciliary beat pattern corresponding to "A1".

In step S6, the processor 1 presents, by the display 3, a heat map to illustrate a spatial distribution of the ciliary beat frequencies corresponding respectively to the target positions that are determined according to all pixels of the N number of denoised images. The heat map has a resolution equal to the video resolution (i.e., 1440×1080 pixels). For each of the target positions, a grayscale value of a pixel of the heat map that corresponds to the target position represents the ciliary beat frequency that corresponds to the target position.

Moreover, the processor 1 presents, by the display 3, a plot illustrating distribution of the ciliary beat frequencies corresponding respectively to the target positions that are determined according to all pixels of the N number of denoised images. The plot has a horizontal axis representing the ciliary beat frequencies, and a vertical axis representing, for each of the ciliary beat frequencies, a number of those of the target positions that corresponds to the ciliary beat frequency. The plot may be one of a histogram, a line chart, a curve chart and a scatter plot, but is not limited to the disclosure herein and may vary in other embodiment.

To sum up, the method according to the disclosure utilizes the processor 1 to determine, for every N number of commonly-located pixels respectively of N number of denoised images, which are derived from a video of ciliary movement, a position of the N number of corresponding pixels are commonly located as a target position when it is determined that N number of grayscale values of the N number of corresponding pixels are not the same. Thereafter, for each target position, the processor 1 is utilized to determine a ciliary beat frequency based on peak values among the N number of grayscale values, and to present, via the display 3, a heat map and a plot that are related to the ciliary beat frequencies thus determined for multiple target positions. In this way, the ciliary beat frequencies may be automatically and efficiently determined.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A method for determining a ciliary beat frequency based on a video of ciliary movement, the video containing a series of consecutive frames, the method comprising steps of:
    determining a frame rate of the video and a video resolution of the video;
    selecting, based on the frame rate, N number of frames from the series of consecutive frames of the video, where N is a positive integer greater than one;
    performing image denoising on the N number of frames to obtain N number of denoised images, respectively, each of the N number of denoised images having a resolution equal to the video resolution;
    determining a plurality of target positions that respectively correspond to a plurality of ciliary beat patterns, wherein, for every N number of commonly-located pixels respectively of the N number of denoised images, when it is determined that N number of grayscale values respectively of the N number of commonly-located pixels are not the same, a position of the N number of commonly-located pixels is determined as one of the target positions, and the N number of grayscale values of the N number of commonly-located pixels at said one of the target positions represent the respective one of the plurality of ciliary beat patterns;
    for each of the ciliary beat patterns, determining peak values among the N number of grayscale values; and
    for each of the ciliary beat patterns, determining a ciliary beat frequency based on the peak values thus determined.

2. The method as claimed in claim 1, wherein the step of selecting N number of frames is to select first N number of consecutive frames of the video.

3. The method as claimed in claim 1, wherein the step of selecting N number of frames is to select N number of consecutive frames of first X seconds of the video, where N is equal to a product of X and the frame rate.

4. The method as claimed in claim 3, wherein the sub-step of performing image smoothing includes, for each pixel of each of the N number of frames, calculating an average of grayscale values respectively of the pixel and surrounding pixels that are located within a predetermined range of the pixel, and replacing a grayscale value of the pixel with the average of grayscale values.

5. The method as claimed in claim 1, wherein the step of performing image denoising includes sub-steps of:
    performing image smoothing on the N number of frames to respectively result in N number of smoothed images;
    for every N number of commonly-located pixels respectively of the N number of smoothed images, determining a position of the N number of commonly-located pixels as a noise position when it is determined that N number of grayscale values respectively of the N number of commonly-located pixels are the same; and
    for each of the N number of frames, replacing a grayscale value of a pixel corresponding to the noise position with a predetermined grayscale value.

6. The method as claimed in claim 1, wherein the step of determining a ciliary beat frequency includes sub-steps of:
    determining, for every consecutive two of the peak vales, an inter-peak time interval between the consecutive two of the peak vales;
    calculating an average of the inter-peak time intervals obtained from all of the peak values; and
    calculating a reciprocal of the average of the inter-peak time intervals as the ciliary beat frequency.

7. The method as claimed in claim 1, further comprising a step of:
    presenting, by a display, a heat map to illustrate a spatial distribution of the ciliary beat frequencies corresponding respectively to the target positions that are determined according to all pixels of the N number of denoised images, the heat map having a resolution equal to the video resolution,
    wherein, for each of the target positions, a grayscale value of a pixel of the heat map that corresponds to the target position represents the ciliary beat frequency that corresponds to the target position.

8. The method as claimed in claim 1, further comprising a step of:
    presenting, by a display, a plot illustrating distribution of the ciliary beat frequencies corresponding respectively to the target positions that are determined according to all pixels of the N number of denoised images, wherein the plot has a horizontal axis representing the ciliary beat frequencies, and a vertical axis representing, for each of the ciliary beat frequencies, a number of those of the target positions that corresponds to the ciliary beat frequency.

9. The method as claimed in claim 8, wherein the step of presenting a plot illustrating distribution of the ciliary beat frequencies is to present one of a histogram, a line chart, a curve chart and a scatter plot.

10. The method as claimed in claim 1, further comprising a step of:
   recording N number of grayscale values of pixels, each of which is located at the target position, respectively of the N number of frames in a matrix.

* * * * *